United States Patent [19]

Bryan et al.

[11] 4,250,143
[45] Feb. 10, 1981

[54] SYSTEM FOR STERILIZING OBJECTS

[75] Inventors: Coleman J. Bryan, Merritt Island; Edward E. Wright, Jr., Titusville; Clyde V. Moyers, Cape Canaveral, all of Fla.

[73] Assignee: The United States of America as represented by the Administrator of the National Aeronautics and Space Administration, Washington, D.C.

[21] Appl. No.: 46,739

[22] Filed: Jun. 8, 1979

[51] Int. Cl.³ .................. A61L 2/08; A61L 9/00; G05D 23/00
[52] U.S. Cl. .................. 422/109; 422/3; 422/27; 422/30; 422/34; 261/79 A
[58] Field of Search .............. 422/109, 111, 120, 123, 422/125, 26, 27, 28–30, 34, 3, 306; 261/79 A, 119 R, 130, 153, DIG. 65

[56] References Cited

U.S. PATENT DOCUMENTS

| | | | |
|---|---|---|---|
| 968,456 | 8/1910 | Edwards | 261/79 A |
| 1,213,887 | 1/1917 | Krause | 261/79 A |
| 2,235,998 | 3/1941 | Kleinschmidt | 261/79 A |
| 2,756,976 | 7/1956 | Jalma | 261/79 A |
| 2,759,713 | 8/1956 | Maniscalo | 261/79 A |
| 3,392,034 | 7/1968 | Barnes | 422/27 |
| 3,767,362 | 10/1973 | Griffin et al. | 422/27 |
| 3,854,468 | 12/1974 | Nozaki | 261/79 A |
| 3,954,406 | 5/1976 | Chamberlain | 422/27 |

FOREIGN PATENT DOCUMENTS

| | | | |
|---|---|---|---|
| 594002 | 3/1960 | Canada | 422/34 |
| 1077246 | 7/1967 | United Kingdom | 422/34 |

OTHER PUBLICATIONS

"Bennett Centrifugal Air Washer", Wilcox-Bennett Carburetor Co., Minneapolis, Minn.

Primary Examiner—William F. Smith
Assistant Examiner—Chris Konkol
Attorney, Agent, or Firm—James O. Harrell; John R. Manning

[57] ABSTRACT

A system for producing a stream of humidified sterilizing gas for sterilizing objects such as the water systems of space vehicles and the like. The system includes a source of sterilant gas which is fed to a mixing chamber having inlet and outlet ports. Water is carried in the mixing chamber with the level of the water only partially filling said mixing chamber so as to provide an empty space adjacent the top of the chamber. A heater is provided for heating the water in said chamber producing a humidified atmosphere. The sterilant gas is fed through an arcuate shaped tubular member connected to the inlet port of the mixing chamber for producing a vortex type of flow of sterilant gas into the chamber for being humidified. A tubular member extends from the mixing chamber for supplying the humidified sterilant gas to the object for being sterilized. Scrubbers are provided for removing the sterilant gas after use.

3 Claims, 2 Drawing Figures

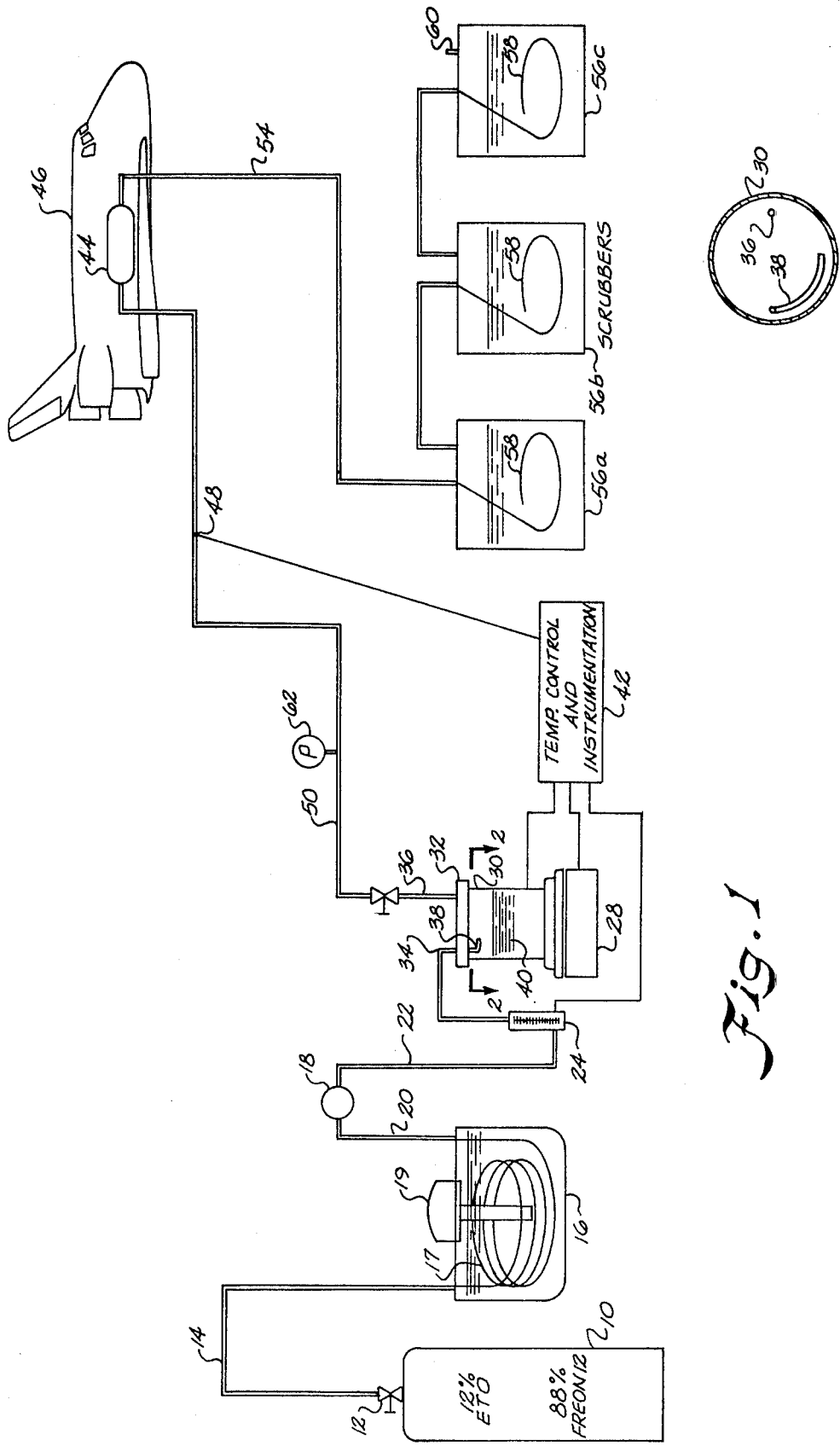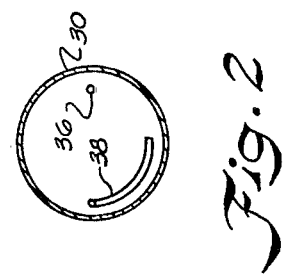

SYSTEM FOR STERILIZING OBJECTS

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

Heretofore, ethylene oxide has been utilized as a sterilizing gas mixture and has been primarily used in a batch type process using a variety of sterilizing autoclaves into which the object or objects to be sterilized are placed. Moisture in the form of steam or water is then introduced in the evacuated autoclave followed by pressurization of the autoclave with the dry ethylene oxide gas mixtures. These processes all rely on gas mixing and diffusing to ensure uniform humidification of the sterilant.

One problem with utilizing autoclaves is that you do not always obtain uniform mixing of the gases. Another problem with utilizing autoclaves is that it is not readily adapted to be used for sterilizing a lot of different objects at different times. Another problem is that between each test, the pressure of the autoclave has to be reduced and the steam mixture of ethylene oxide and water has to be evacuated. Between each sterilization, the water carried in the bottom of the autoclave must be reheated to generate the steam for mixing with a new supply of ethylene oxide mixture.

To be an effective sterilant, ethylene oxide gas should be humidified to between 40% to 80% relative humidity throughout the system to be sterilized. Because of the many dead end cavities, tanks and long runs of small diameter tubing existing in an integrated system, continuous humidification of the ethylene oxide/Freon 12 mixture is necessary as the evacuated system is filled and pressurized to 20 to 22 p.s.i. with the sterilant. This ensures that all areas of the system are contacted with humidified sterilant.

Examples of apparatus and methods of controlling the relative humidity of gaseous sterilizers and sterilizing equipment are disclosed in United States Pat. Nos. 3,687,612, 3,791,424, 3,767,362, 3,620,265, 3,897,210 and 3,851,043.

SUMMARY OF THE INVENTION

The invention includes a system which can be readily used for sterilizing relatively inaccessible objects such as water tanks and water lines with a continuous supply of a pressurized sterilizing gas mixture. The system would be particularly adaptable for sterilizing the water systems and tubes leading to the water systems of space vehicles such as a space shuttle prior to use or reuse. It could also be readily used in municipalities for sterilization of water systems and in hospitals, clinics, biological testing laboratories, and other environments which require sterilization.

The system includes a source of sterilizing gas mixture such as 12% ethylene oxide/88% Freon-12 that is carried within a pressurized container. The pressurized gas mixture is fed through a heated coil for ensuring that the mixture is converted from a liquid state to a gaseous state. A mixing chamber is provided having a heater positioned adjacent the bottom thereof and a water level which only partially fills the chamber so as to provide an empty space adjacent the top of the chamber. The gas mixture is fed into the mixing chamber through an arcuate tubular member so as to produce a vortex type of flow within the empty space of the chamber. While in the chamber, the gas mixture is humidified to between 40% and 80% relative humidity. Connected to the output of the mixing chamber is a tubular member that can be readily connected to the object to be sterilized such as the water system in a space shuttle. A return tubular member is also connected to the object being sterilized and fed through a plurality of scrubbers which remove the ethylene oxide prior to venting to the atmosphere.

Accordingly, it is an important object of the present invention to provide a system for producing a gaseous mixture of ethylene oxide and water according to a predetermined percentage so as to be an effective sterilant.

Another important object of the present invention is to provide a system for producing a gas mixture of ethylene oxide which is humidified to a relative humidity of approximately 40% to 80% producing a continuous supply of sterilizing gas for sterilizing objects that are relatively inaccessible.

Another important object of the present invention is to provide a system for sterilizing objects which cannot be readily placed within containers such as sterilizing autoclaves.

Still another important object of the present invention is to provide a system for producing a sterilizing gas mixture of a predetermined relative humidity that can be readily controlled.

These and other objects and advantages of the invention will become apparent upon reference to the following specification, attendant claims and drawing.

BRIEF DESCRIPTION OF THE DRAWING

FIG. 1 is a flow diagram illustrating a system for producing a continuous flow of sterilizing gas constructed in accordance with the present invention;

FIG. 2 is a sectional view taken along line 2—2 of FIG. 1 illustrating an arcuate member for conveying the gaseous mixture within a mixing chamber.

DESCRIPTION OF THE PREFERRED EMBODIMENT

Referring in more detail to FIG. 1 of the drawing, there is illustrated a commercial tank 10 of ethylene oxide and freon having a ratio of 12% ethylene oxide and 88% Freon-12. Normally, the mixture is in a liquid state maintained under pressure. Connected to the tank 10 is a valve 12 which controls the flow of the liquid from the pressurized tank 10. The pressurized liquid flows through a tube 14 into a heater water bath 16. The heated water bath 16 includes a coil of tubing 17 that is directly connected to the tube 14. Water is carried within the bath 16 and a heater 19 is provided for heating the water to a predetermined temperature to ensure that the liquid entering the coiled tubular member 17 is converted to a gaseous state. Connected to an exit end of the coil tube 17 is a pressure regulator 18 which is adjustable for regulating the pressure of the gas flowing through tubes 20 and 22 extending from the water bath to a flow temperature meter 24. The flow temperature meter 24 measures the rate of flow of the sterilant gas therethrough as well as the temperature of the gas.

A mixing chamber 26 is provided for receiving the gas mixture from the flow temperature meter 24 and includes a hot plate 28 upon which a vessel 30 is carried. A top 32 is provided on the vessel 30 and has an inlet port 34 provided therein as well as an exit port 36. Connected to the inlet port 34 is an arcuate shaped member 38 which extends down into an empty space provided between the top of the water level 40 and the top 32 of the vessel. The arcuate shaped tubular member 38 produces a vortex type of flow around the vessel so as to provide efficient mixing of the ethylene oxide/Freon gas with water vapor provided in the empty space.

The temperature of the heater or hot plate 28 can be varied for controlling the percent of humidification of the ethylene oxide/Freon mixture. A temperature control and instrumentation circuit 42 is provided for controlling and sensing the flow and temperature of the gas flowing through the meter 24, the temperature of the water 40 carried within the vessel 30, and the humidity and temperature of the humidified gaseous mixture entering the object being sterilized. As illustrated schematically in FIG. 1, the object being sterilized is a water tank 44 provided in a space shuttle 46. A temperature and humidity sensor 48 is interposed in a line 50 leading to the water tank. The line 50 is, in turn, directly connected to the outlet port 36 of the mixing chamber.

The sensing probe 48 sends a signal back to the temperature control and instrumentation circuit 42 so that the system can be adjusted for maintaining the desired amount of humidity in the gaseous mixture.

The gaseous mixture, after sterilizing the water system 44 of the space shuttle 46, is fed into a scrubber by means of tube 54. The scrubber includes three vessels, 56a, 56b, and 56c. Each of these vessels include a perforated coil tube 58 and is filled with a solution of 1/10 molar sulphuric acid. As the sterilizing mixture is bubbled through the solution carried in the scrubber, it is absorbed therein. In order to ensure that all of the gaseous mixture is absorbed, the vessels 56a through 56c are connected in series so that the output of vessel 56a is connected to the coil member 58 of vessel 56b and the output of the vessel 56b is, in turn, connected to the coil tubular member 58 of vessel 56c. In each of these vessels, the gaseous mixture is bubbled through the solution prior to exiting that particular vessel. The output of vessel 56 c is vented to the atmosphere through a vent 60.

A pressure regulator 62 is interposed in the tubular member 50 extending between the mixing chamber 26 and the object being sterilized so as to regulate and maintain the proper pressure of the sterilizing gas during the sterilizing process. As a result of the mixing chamber producing a continuous stream of sterilizing gas, the tubular member 50 can be readily connected to any object that is desired to be sterilized such as water pipes, vessels, water systems, etc.

In FIG. 2, the arcuate shaped tubular member 38 is illustrated showing the direction that the sterilant gas takes when entering the mixing chamber. As a result of the liquid gas assuming a vortex type of flow around the empty space of the mixing chamber, the degree of humidification of the gas it is mixing can be readily controlled.

While a preferred embodiment of the invention has been described using specific terms, such description is for illustrative purposes only, and it is to be understood that changes and variations may be made without departing from the spirit or scope of the following claims.

What is claimed is:

1. A system for producing a humidified sterilizing gas mixture for sterilizing an object comprising:
    (a) means for supplying a pressurized sterilant gas;
    (b) a mixing chamber having a closed top and bottom;
    (c) inlet and outlet ports provided in said top of said mixing chamber;
    (d) water carried in said mixing chamber with the level of said water only partially filling said mixing chamber so as to provide an empty space adjacent the top of the chamber;
    (e) a hot plate heating said water in said chamber to a predetermined temperature producing a humidified atmosphere in said empty space;
    (f) means for feeding said sterilant gas through said inlet port;
    (g) an arcuate shaped elongated tube connected to said inlet port and extending into said empty space of said chamber for producing a vortex type of flow of sterilant gas in said chamber through said humidified atmosphere so as to be humidified;
    (h) tubular means connected to said outlet port for conveying said humidified sterilant gas to said object for sterilizing said object,
    (i) a temperature and humidity sensor carried in said tubular means connected to said outlet port;
    (j) temperature and humidity control means connected to said temperature and humidity sensor, said mixing chamber, and said hot plate for maintaining said humidified sterilizing gas at a predetermined degree of relative humidity.

2. The system as set forth in claim 1 further comprising:
    said means for supplying sterilant gas including:
        (i) a pressurized tank of ethylene oxide/Freon 12 in a liquid state,
        (ii) a heater,
        (iii) tubular means supplying said ethylene oxide/Freon 12 from said tank to said heater for converting said ethylene oxide/Freon 12 from a liquid state to a gaseous state.

3. The system as set forth in claim 1 further comprising:
    a plurality of scrubbers connected to said object being sterilized for receiving exhaust gases from said object; and
    a gas absorbing solution carried in said scrubbers for removing said sterilant gas from said humidified gas mixture.

* * * * *